United States Patent
O'Brien et al.

(10) Patent No.: US 8,642,757 B2
(45) Date of Patent: Feb. 4, 2014

(54) HIGH TITER PRODUCTION OF HIGHLY LINEAR POLY (α 1,3 GLUCAN)

(75) Inventors: John P O'Brien, Oxford, PA (US);
Mark S Payne, Wilmington, DE (US)

(73) Assignee: E I du pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/606,373

(22) Filed: Sep. 7, 2012

(65) Prior Publication Data
US 2013/0244287 A1    Sep. 19, 2013

Related U.S. Application Data

(60) Provisional application No. 61/532,723, filed on Sep. 9, 2011.

(51) Int. Cl.
*C07H 1/00*  (2006.01)
*C13K 5/00*  (2006.01)
*A61K 38/46* (2006.01)

(52) U.S. Cl.
USPC ............. 536/126; 536/123.1; 424/94.6

(58) Field of Classification Search
USPC ............... 536/123.1, 126; 424/94.6
See application file for complete search history.

(56) References Cited

U.S. PATENT DOCUMENTS 4,501,886 A   2/1985   O'Brien
7,000,000 B1  2/2006   O'Brien

OTHER PUBLICATIONS

Ogawa et al., Crystal Structure of (1->3)-Alpha-D-Glucan, in Fiber Diffraction Methods, French, A., et al., ACS Symposium Series, American Chemical Society, Washington, D.C. (1980), pp. 353-362.
Simpson et al., Four Glucosyltransferases, GTFJ, GTFK, GTFL, and GTFM, From *Streptococcus salivarius* ATCC 25975, Microbiology, vol. 141 (1995), pp. 1451-1460.
International Search Report, Corresponding PCT International Patent Application No. PCT/US2012/054435, Mailed September 24, 2013.
Kingston et al., Role of the C-Terminal Yg Repeats of the Primer-Dependent Streptococcal Glucosyltransferase, GTFJ, in Binding to Dextran and Mutan, Microbiology, Vol. 148, No. 2 (2001), pp. 549-558.
Simpson et al., Four Glucosyltransferases, GTFJ, GTFK, GTFL, and GTFM From Streptococcus Salivarious ATCC 25975, Microbiology and Immunology, Vol. 141, No. 6 (1995), pp. 1451-1460.
Haas et al., Ligand-Binding Properties of the Carboxyl-Terminal Repeat Domain of Streptococcus Mutans Glucan-Binding Protein A, Journal of Bacteriology, Vol. 182, No. 3 (2000) pp. 728-733.
Argimon et al., Phylogenetic Analysis of Glucosyltransferases and Implications for the Coevolution of Mutans Streptococci With Their Mammalian Hosts, Plos One, Vol. 8, No. 2, E56305 (2013), pp. 1-11.

*Primary Examiner* — Maryam Monshipouri

(57) ABSTRACT

A process for enzymatic preparation of a highly linear poly (α1,3 glucan) from sucrose is disclosed. The glucosyltransferase enzyme (gtfJ) from *Streptococcus salivarius* is used to convert sucrose to a highly linear poly(α1,3 glucan) in high titers. Hydrolyzed poly(α1,3 glucan) is used as the primer for the gtfJ enzyme reaction resulting in the formation of highly linear poly(α1,3 glucan).

17 Claims, 2 Drawing Sheets

SEQUENCE LISTING

```
<160> NUMBER OF SEQ ID NOS: 3

<210> SEQ ID NO 1
<211> LENGTH: 4434
<212> TYPE: DNA
<213> ORGANISM: artificial sequence
<220> FEATURE:
<223> OTHER INFORMATION: codon-optimized gtfj gene from Streptococcus
      salivarius

<400> SEQUENCE: 1
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacggatgct ccggcggtca cgaccgagaa agcggaagaa     300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540
accccaggca ctaccaatat cgtggacggt tttagcatta caaccgcgc ttacgacagc     600 agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagttttca acctggacgc gaaatactct agcaccgaca aacaggaaac cctgaaagtg     840
gcagcaaaag acattcaaat caagattgaa caaaagattc aagcggagaa gagcacgcag     900
tggctgcgtg aaactatcag cgcctttgtg aaaacccagc cgcagtggaa caaagaaacc     960
gagaattaca gcaagggtgg tggtgaggac cacctgcaag gtggcgcact gctgtatgtt    1020
aacgacagcc gtaccccttg ggcgaatagc gattaccgtc gtctgaatcg caccgcaacc    1080
aatcagacgg gcacgatcga taagtctatt ctggacgagc agtctgaccc aaaccacatg    1140
ggcggtttcg actttctgct ggcgaacgac gtcgacctga gcaatccggt cgtgcaggct    1200
gagcagctga atcaaatcca ctatctgatg aatttggggtt ccattgtgat gggtgacaag    1260
gatgcgaact tgacggcat tcgtgtcgat gcagttgaca acgtggacgc ggacatgttg    1320
caactgtata ccaattactt ccgtgagtac tacggtgtga acaagagcga agctaacgca    1380
```

```
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagagcg taccccggca gtgagcccgc tgtataacaa caccttcaat    1560
accacccagc gtgatgaaaa gaccgattgg attaacaaag acggtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtataccctg    1860
aataacattc cggcagcgta tgccgtgatg ttgcagaata tggaaacgat acccgcgtc    1920 tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct tggtcgcgaa caatccgaag    2220
ctgaatctgg accaaagcgc caagttgaat gtggagatgg gcaaaatcca tgcgaatcag    2280
aagtatcgcg cactgattgt cggcactgcg gacggcatta agaactttac ttccgacgcg    2340
gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata ccagctgat ttacgaaggc    2580 tttagcaatt ccagacgat cccagatggc agcgatccgt ccgtgtatac gaaccgcaag    2640
attgcggaga acgtggatct gttcaaaagc tggggtgtca ccagctttga gatggcaccg    2700
caatttgtct cggcggatga tggcaccttt ctggatagcg ttattcagaa tggctacgcc    2760
ttcgccgacc gttatgacct ggccatgtcc aagaacaaca agtatggtag caaagaggac    2820
ctgcgtgatg cactgaaagc actgcataag gcgggtattc aagctatcgc agactgggtt    2880
ccagaccaga tctaccagct gccgggcaaa gaagttgtca ccgccacccg tacgatggt    2940 gctggccgta agatcgcaga cgcgattatc gaccattctc tgtatgttgc aaacagcaaa    3000
agcagcggca agattatca agcaaagtac ggtggcgagt tcctggccga gctgaaagcc    3060 aaataccccgg aaatgttcaa agttaacatg attagcacgg gtaagccgat tgatgactcc    3120
gtgaaattga agcaatggaa agccgagtac ttcaatggca ccaacgtttt ggaacgtggt    3180
gtcggctatg ttctgagcga cgaggcgacc ggtaagtatt tcacggtgac caaagaaggc    3240 aattcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg gcaaggacgt ctaccgtttt ctgccgaacg tatcatgct gagcaatgcg    3480 ttttacattg atgcgaacgg taataccatc ctgtacaact ctaagggtca aatgtacaaa    3540
ggcggttaca cgaaattcga tgtttctgaa acggataaga acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
```

-continued

| | |
|---|---|
| aatatcaatg gtaaatggta ctatttcgac gcgaatggcg ttgctgcgac cggtgcgcag | 3840 |
| gtgattaacg gccagaaact gtacttcaac gaggatggct cccaagtcaa aggcggcgtg | 3900 |
| gttaagaacg cagacggcac ctatagcaaa tacaaagaag gttttggtga gctggttact | 3960 |
| aacgagtttt tcacgactga tggcaatgtt tggtactacg ccggtgcaaa tggtaaaacc | 4020 |
| gttaccggtg cacaagtgat caacggccaa catttgtact tcaatgcgga cggttcccag | 4080 |
| gtgaagggtg gcgttgtcaa gaacgcggat ggcacctaca gcaagtacaa tgctagcact | 4140 |
| ggtgaacgtc tgacgaacga gttctttacg accggtgata acaattggta ttacattggc | 4200 |
| gcaaacggta gagcgtgac gggtgaggtc aagattggtg atgatactta cttttcgcg | 4260 |
| aaggatggca acaagttaa aggtcaaacc gtcagcgccg gtaatggtcg cattagctac | 4320 |
| tactacggtg acagcggcaa gcgtgcggtt agcacctgga ttgagattca gccgggtgtt | 4380 |
| tatgtgtatt tcgacaaaaa cggtttggcg taccctccgc gtgttctgaa ttaa | 4434 |

<210> SEQ ID NO 2
<211> LENGTH: 8455
<212> TYPE: DNA
<213> ORGANISM: artificial sequence
<220> FEATURE:
<223> OTHER INFORMATION: plasmid pMP52

<400> SEQUENCE: 2

| | |
|---|---|
| ctcatgacca aaatccctta acgtgagtta cgcgcgcgtc gttccactga gcgtcagacc | 60 |
| ccgtagaaaa gatcaaagga tcttcttgag atcctttttt tctgcgcgta atctgctgct | 120 |
| tgcaaacaaa aaaaccaccg ctaccagcgg tggtttgttt gccggatcaa gagctaccaa | 180 |
| ctcttttttcc gaaggtaact ggcttcagca gagcgcagat accaaatact gttcttctag | 240 |
| tgtagccgta gttagcccac cacttcaaga actctgtagc accgcctaca tacctcgctc | 300 |
| tgctaatcct gttaccagtg gctgctgcca gtggcgataa gtcgtgtctt accgggttgg | 360 |
| actcaagacg atagttaccg gataaggcgc agcggtcggg ctgaacgggg ggttcgtgca | 420 |
| cacagcccag cttggagcga acgacctaca ccgaactgag atacctacag cgtgagctat | 480 |
| gagaaagcgc cacgcttccc gaagggagaa aggcggacag gtatccggta agcggcaggg | 540 |
| tcggaacagg agagcgcacg agggagcttc caggggaaa cgcctggtat ctttatagtc | 600 |
| ctgtcgggtt tcgccacctc tgacttgagc gtcgattttt gtgatgctcg tcagggggc | 660 |
| ggagcctatg gaaaaacgcc agcaacgcgg cctttttacg gttcctggcc ttttgctggc | 720 |
| cttttgctca catgttcttt cctgcgttat ccctgattc tgtggataac cgtattaccg | 780 |
| cctttgagtg agctgatacc gctcgccgca gccgaacgac cgagcgcagc gagtcagtga | 840 |
| gcgaggaagc ggaaggcgag agtagggaac tgccaggcat caaactaagc agaaggcccc | 900 |
| tgacggatgg cctttttgcg tttctacaaa ctctttctgt gttgtaaaac gacggccagt | 960 |
| cttaagctcg ggcccctgg gcggttctga taacgagtaa tcgttaatcc gcaaataacg | 1020 |
| taaaacccg cttcggcggg ttttttatg gggggagttt agggaaagag catttgtcag | 1080 |
| aatatttaag ggcgcctgtc actttgcttg atatatgaga attatttaac cttataaatg | 1140 |
| agaaaaaagc aacgcacttt aaataagata cgttgctttt tcgattgatg aacacctata | 1200 |
| attaaactat tcatctatta tttatgattt tttgtatata caatatttct agtttgttaa | 1260 |
| agagaattaa gaaataaat ctcgaaaata ataagggaa aatcagtttt tgatatcaaa | 1320 |
| attatacatg tcaacgataa tacaaaatat aatacaaact ataagatgtt atcagtatt | 1380 |
| attatgcatt tagaataaat tttgtgtcgc ccttaattgt gagcggataa caattacgag | 1440 |

```
cttcatgcac agtgaaatca tgaaaaattt atttgctttg tgagcggata acaattataa    1500
tatgtggaat tgtgagcgct cacaattcca caacggtttc cctctagaaa taattttgtt    1560
taacttttga attctctaga ggaaggtaaa acatatggac gaaacgcagg ataagaccgt    1620
gacgcagagc aacagcggca ccaccgcttc cctggtcact agccctgaag ccacgaaaga    1680
ggcggacaaa cgcacgaaca ctaaagaggc cgacgttctg acgcctgcaa agaaacgaa     1740 cgcagtcgag actgcgacca ccactaacac ccaggcgacg gcggaggccg ccacgaccgc    1800
gaccaccgcg gacgtcgcgg tggctgcggt gccgaacaaa gaagcggtcg ttaccacgga    1860
tgctccggcg gtcacgaccg agaaagcgga agaacagccg gctaccgtta aagcagaagt    1920
cgtcaatacg gaagtgaaag cgccggaagc ggctctgaaa gacagcgagg ttgaggcagc    1980
gctgagcctg aagaacatca agaacattga tggcaagtat tactatgtta atgaggatgg    2040
cagccacaaa gagaatttcg ctattaccgt gaatggccag ctgctgtact ttggtaaaga    2100
cggtgcgctg acgtcctcta gcacgtattc ttttaccccca ggcactacca atatcgtgga    2160
cggttttagc attaacaacc gcgcttacga cagcagcgag gcgagctttg agctgatcga    2220
cggttacttg accgcagaca gctggtatcg tccggctagc atcatcaaag atggtgttac    2280
gtggcaagcg tccaccgccg aggattttcg tccgctgctg atggcatggt ggccgaatgt    2340
ggatacgcag gtgaactatt tgaattacat gtccaaagtt ttcaacctgg acgcgaaata    2400
ctctagcacc gacaaacagg aaaccctgaa agtggcagca aaagacattc aaatcaagat    2460
tgaacaaaag attcaagcgg agaagagcac gcagtggctg cgtgaaacta tcagcgcctt    2520
tgtgaaaacc cagccgcagt ggaacaaaga aaccgagaat tacagcaagg gtggtggtga    2580
ggaccacctg caaggtggcg cactgctgta tgttaacgac agccgtaccc cttgggcgaa    2640
tagcgattac cgtcgtctga atcgcaccgc aaccaatcag acgggcacga tcgataagtc    2700
tattctggac gagcagtctg acccaaacca catgggcggt ttcgactttc tgctggcgaa    2760
cgacgtcgac ctgagcaatc cggtcgtgca ggctgagcag ctgaatcaaa tccactatct    2820
gatgaattgg ggttccattg tgatgggtga caaggatgcg aactttgacg gcattcgtgt    2880
cgatgcagtt gacaacgtgg acgcggacat gttgcaactg tataccaatt acttccgtga    2940
gtactacggt gtgaacaaga gcgaagctaa cgcactggct cacatcagcg ttctggaggc    3000
gtggagcctg aatgataatc attacaatga caagaccgat ggtgcggcac tggcaatgga    3060
gaataagcaa cgtctggcgc tgttgttttc gttggcgaaa ccgatcaaag agcgtacccc    3120
ggcagtgagc ccgctgtata caacaccttt caataccacc cagcgtgatg aaaagaccga    3180
ttggattaac aaagacggta gcaaggctta caacgaagat ggcacggtca acaatcgac     3240 catcggtaag tacaacgaga atacggtga cgcatccggt aactacgttt tcatccgtgc     3300
ccacgataac aacgtccagg acatcatcgc cgagatcatc aagaaagaga tcaacccgaa    3360
aagcgacggc ttcaccatca ccgacgccga aatgaagcaa gcctttgaaa tctataacaa    3420
agatatgctg tcgagcgaca aaagtatac cctgaataac attccggcag cgtatgccgt     3480
gatgttgcag aatatggaaa cgattacccg cgtctattac ggtgatctgt atacggacga    3540
cggtcactac atggaaacca aatctccgta ttacgatacc atcgtgaatt tgatgaagag    3600
ccgtatcaag tatgtttcgg gtggccaggc gcaacgtagc tattggctgc cgaccgacgg    3660
taagatggac aatagcgacg ttgagctgta ccgcacgaat gaggtttaca cgagcgtgcg    3720
ctatggtaag gatatcatga ccgctaatga taccgaaggc tctaagtatt cccgcaccag    3780
cggccaagtc accttggtcg cgaacaatcc gaagctgaat ctggaccaaa gcgccaagtt    3840
```

```
gaatgtggag atgggcaaaa tccatgcgaa tcagaagtat cgcgcactga ttgtcggcac    3900
tgcggacggc attaagaact ttacttccga cgcggacgcc attgcagcgg gttatgtgaa    3960
agaaaccgat agcaacggcg tgctgacctt cggtgctaac gacattaagg gctacgaaac    4020
gtttgatatg agcggtttcg tggcggtgtg ggttccggtg ggtgcatctg acaatcagga    4080
cattcgtgtt gcgccgagca ccgaggcaaa gaaagaaggt gagctgacct tgaaggcgac    4140
ggaagcgtat gatagccagc tgatttacga aggctttagc aatttccaga cgatcccaga    4200
tggcagcgat ccgtccgtgt atacgaaccg caagattgcg gagaacgtgg atctgttcaa    4260
aagctggggt gtcaccagct tgagatggc accgcaattt gtctcggcgg atgatggcac    4320
ctttctggat agcgttattc agaatggcta cgccttcgcc gaccgttatg acctggccat    4380
gtccaagaac aacaagtatg gtagcaaaga ggacctgcgt gatgcactga aagcactgca    4440
taaggcgggt attcaagcta tcgcagactg ggttccagac cagatctacc agctgccggg    4500
caaagaagtt gtcaccgcca cccgtacgga tggtgctggc cgtaagatcg cagacgcgat    4560
tatcgaccat tctctgtatg ttgcaaacag caaaagcagc ggcaaagatt atcaagcaaa    4620
gtacggtggc gagttcctgg ccgagctgaa agccaaatac ccggaaatgt tcaaagttaa    4680
catgattagc acgggtaagc cgattgatga ctccgtgaaa ttgaagcaat ggaaagccga    4740
gtacttcaat ggcaccaacg ttttggaacg tggtgtcggc tatgttctga gcgacgaggc    4800
gaccggtaag tatttcacgg tgaccaaaga aggcaatttc attccgctgc aactgacggg    4860
taaagagaaa gttatcacgg gtttctccag cgatggtaag ggtatcacct atttcggtac    4920
gagcggtacg caggcgaagt ctgcgtttgt taccttcaat ggtaacacct actatttcga    4980
cgcgcgtggc cacatggtta ccaatagcga atacagcccg aatggcaagg acgtctaccg    5040
ttttctgccg aacggtatca tgctgagcaa tgcgttttac attgatgcga acggtaatac    5100
ctacctgtac aactcaagg gtcaaatgta caaaggcggt tacacgaaat tcgatgtttc    5160
tgaaacggat aaggacggta aagagtccaa ggtcgtcaag ttccgctact ttacgaacga    5220
aggcgtcatg gccaagggtg ttaccgtcat tgatggtttt acccaatact tcggtgagga    5280 cggcttttcaa gcgaaggata agctggtcac cttcaagggc aagacgtatt acttcgacgc    5340
acacactggt aatggtatca agatacctg gcgcaatatc aatggtaaat ggtactattt    5400
cgacgcgaat ggcgttgctg cgaccggtgc gcaggtgatt aacggccaga aactgtactt    5460
caacgaggat ggctcccaag tcaaaggcgg cgtggttaag aacgcagacg gcacctatag    5520
caaatacaaa gaaggttttg gtgagctggt tactaacgag tttttcacga ctgatggcaa    5580
tgtttggtac tacgccggtg caaatggtaa aaccgttacc ggtgcacaag tgatcaacgg    5640
ccaacatttg tacttcaatg cggacggttc ccaggtgaag ggtggcgttg tcaagaacgc    5700
ggatggcacc tacagcaagt acaatgctag cactggtgaa cgtctgacga acgagttctt    5760
tacgaccggt gataacaatt ggtattacat tggcgcaaac ggtaagagcg tgacgggtga    5820
ggtcaagatt ggtgatgata cttactttt cgcgaaggat ggcaaacaag ttaaaggtca    5880
aaccgtcagc gccggtaatg tcgcattag ctactactac ggtgacagcg gcaagcgtgc    5940
ggttagcacc tggattgaga ttcagccggg tgtttatgtg tatttcgaca aaaacgtttt    6000
ggcgtaccct ccgcgtgttc tgaattaatg agtctagact gcagggtacc aagcttcccc    6060
aagggcgaca ccccataatt agcccgggcg aaaggcccag tctttcgact gagccttcg    6120 tttatttga tgcctggcag ttccctactc tcgcatgggg agtccccaca ctaccatcgg    6180
cgctacggcg tttcacttct gagttcggca tggggtcagg tgggaccacc gcgctactgc    6240
```

```
cgccaggcaa acaagggtg ttatgagcca tattcaggta taaatgggct cgcgataatg   6300
ttcagaattg gttaattggt tgtaacactg acccctattt gtttattttt ctaaatacat   6360
tcaaatatgt atccgctcat gagacaataa ccctgataaa tgcttcaata atattgaaaa   6420
aggaagaata tgagtattca acatttccgt gtcgcccta ttcctttttt tgcggcattt    6480
tgccttcctg tttttgctca cccagaaacg ctggtgaaag taaaagatgc tgaagatcag   6540
ttgggtgcac gagtgggtta catcgaactg gatctcaaca gcggtaagat ccttgagagt   6600
tttcgccccg aagaacgttt tccaatgatg agcacttta aagttctgct atgtggcgcg    6660
gtattatccc gtattgacgc cgggcaagag caactcggtc gccgcataca ctattctcag   6720
aatgacttgg ttgagtactc accagtcaca gaaaagcatc ttacggatgg catgacagta   6780
agagaattat gcagtgctgc cataaccatg agtgataaca ctgcggccaa cttacttctg   6840
acaacgatcg gaggaccgaa ggagctaacc gcttttttgc acaacatggg ggatcatgta   6900
actcgccttg atcgttggga accggagctg aatgaagcca taccaaacga cgagcgtgac   6960
accacgatgc ctgtagcgat ggcaacaacg ttgcgcaaac tattaactgg cgaactactt   7020
actctagctt cccggcaaca attaatagac tggatggagg cggataaagt tgcaggacca   7080
cttctgcgct cggcccttcc ggctggctgg tttattgctg ataaatccgg agccggtgag   7140
cgtggttctc gcggtatcat cgcagcgctg gggccagatg gtaagccctc ccgtatcgta   7200
gttatctaca cgacggggag tcaggcaact atggatgaac gaaatagaca gatcgctgag   7260
ataggtgcct cactgattaa gcattggtaa gcggcgcgcc atcgaatggc gcaaaacctt   7320
tcgcggtatg gcatgatagc gcccggaaga gagtcaattc agggtggtga atatgaaacc   7380
agtaacgtta tacgatgtcg cagagtatgc cggtgtctct tatcagaccg tttcccgcgt   7440
ggtgaaccag gccagccacg tttctgcgaa aacgcgggaa aaagtggaag cggcgatggc   7500
ggagctgaat tacattccca accgcgtggc acaacaactg gcgggcaaac agtcgttgct   7560
gattggcgtt gccacctcca gtctggccct gcacgcgccg tcgcaaattg tcgcggcgat   7620
taaatctcgc gccgatcaac tgggtgccag cgtggtggtg tcgatggtag aacgaagcgg   7680
cgtcgaagcc tgtaaagcgg cggtgcacaa tcttctcgcg caacgcgtca gtgggctgat   7740
cattaactat ccgctggatg accaggatgc cattgctgtg gaagctgcct gcactaatgt   7800
tccggcgtta tttcttgatg tctctgacca gacacccatc aacagtatta ttttctccca   7860
tgaggacggt acgcgactgg gcgtggagca tctggtcgca ttgggtcacc agcaaatcgc   7920
gctgttagcg ggcccattaa gttctgtctc ggcgcgtctg cgtctggctg ctggcataa    7980 atatctcact cgcaatcaaa ttcagccgat agcggaacgg gaaggcgact ggagtgccat   8040
gtccggtttt caacaaacca tgcaaatgct gaatgagggc atcgttccca ctgcgatgct   8100
ggttgccaac gatcagatgg cgctgggcgc aatgcgcgcc attaccgagt ccgggctgcg   8160
cgttggtgcg gatatctcgg tagtgggata cgacgatacc gaagatagct catgttatat   8220
cccgccgtta accaccatca aacaggattt tcgcctgctg gggcaaacca gcgtggaccg   8280
cttgctgcaa ctctctcagg gccaggcggt gaagggcaat cagctgttgc cagtctcact   8340
ggtgaaaaga aaaaccaccc tggcgcccaa tacgcaaacc gcctctcccc gcgcgttggc   8400
cgattcatta atgcagctgg cacgacaggt ttcccgactg gaaagcgggc agtga         8455
```

<210> SEQ ID NO 3
<211> LENGTH: 1518
<212> TYPE: PRT
<213> ORGANISM: Streptococcus salivarius

<400> SEQUENCE: 3

```
Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
            20                  25                  30

Leu Ser Val Thr Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
        355                 360                 365

Gly Glu Asp His Leu Gln Gly Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415
```

```
Asp Pro Asn His Met Gly Gly Phe Asp Phe Leu Leu Ala Asn Asp Val
        420                 425                 430

Asp Leu Ser Asn Pro Val Val Gln Ala Glu Gln Leu Asn Gln Ile His
            435                 440                 445

Tyr Leu Met Asn Trp Gly Ser Ile Val Met Gly Asp Lys Asp Ala Asn
        450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
                500                 505                 510

Leu Asn Asp Asn His Tyr Asn Asp Lys Thr Asp Gly Ala Ala Leu Ala
            515                 520                 525

Met Glu Asn Lys Gln Arg Leu Ala Leu Leu Phe Ser Leu Ala Lys Pro
        530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
        595                 600                 605

Arg Ala His Asp Asn Asn Val Gln Asp Ile Ile Ala Glu Ile Ile Lys
610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Asn Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
```

-continued

```
            835                 840                 845
Glu Thr Phe Asp Met Ser Gly Phe Val Ala Val Trp Val Pro Val Gly
850                 855                 860
Ala Ser Asp Asn Gln Asp Ile Arg Val Ala Pro Ser Thr Glu Ala Lys
865                 870                 875                 880
Lys Glu Gly Glu Leu Thr Leu Lys Ala Thr Glu Ala Tyr Asp Ser Gln
                885                 890                 895
Leu Ile Tyr Glu Gly Phe Ser Asn Phe Gln Thr Ile Pro Asp Gly Ser
                900                 905                 910
Asp Pro Ser Val Tyr Thr Asn Arg Lys Ile Ala Glu Asn Val Asp Leu
                915                 920                 925
Phe Lys Ser Trp Gly Val Thr Ser Phe Glu Met Ala Pro Gln Phe Val
            930                 935                 940
Ser Ala Asp Asp Gly Thr Phe Leu Asp Ser Val Ile Gln Asn Gly Tyr
945                 950                 955                 960
Ala Phe Ala Asp Arg Tyr Asp Leu Ala Met Ser Lys Asn Asn Lys Tyr
                965                 970                 975
Gly Ser Lys Glu Asp Leu Arg Asp Ala Leu Lys Ala Leu His Lys Ala
                980                 985                 990
Gly Ile Gln Ala Ile Ala Asp Trp Val Pro Asp Gln Ile Tyr Gln Leu
                995                 1000                1005
Pro Gly Lys Glu Val Val Thr Ala Thr Arg Thr Asp Gly Ala Gly
        1010                1015                1020
Arg Lys Ile Ala Asp Ala Ile Asp His Ser Leu Tyr Val Ala
        1025                1030                1035
Asn Ser Lys Ser Ser Gly Lys Asp Tyr Gln Ala Lys Tyr Gly Gly
        1040                1045                1050
Glu Phe Leu Ala Glu Leu Lys Ala Lys Tyr Pro Glu Met Phe Lys
        1055                1060                1065
Val Asn Met Ile Ser Thr Gly Lys Pro Ile Asp Asp Ser Val Lys
        1070                1075                1080
Leu Lys Gln Trp Lys Ala Glu Tyr Phe Asn Gly Thr Asn Val Leu
        1085                1090                1095
Glu Arg Gly Val Gly Tyr Val Leu Ser Asp Glu Ala Thr Gly Lys
        1100                1105                1110
Tyr Phe Thr Val Thr Lys Glu Gly Asn Phe Ile Pro Leu Gln Leu
        1115                1120                1125
Thr Gly Lys Glu Lys Val Ile Thr Gly Phe Ser Ser Asp Gly Lys
        1130                1135                1140
Gly Ile Thr Tyr Phe Gly Thr Ser Gly Thr Gln Ala Lys Ser Ala
        1145                1150                1155
Phe Val Thr Phe Asn Gly Asn Thr Tyr Phe Asp Ala Arg Gly
        1160                1165                1170
His Met Val Thr Asn Ser Glu Tyr Ser Pro Asn Gly Lys Asp Val
        1175                1180                1185
Tyr Arg Phe Leu Pro Asn Gly Ile Met Leu Ser Asn Ala Phe Tyr
        1190                1195                1200
Ile Asp Ala Asn Gly Asn Thr Tyr Leu Tyr Asn Ser Lys Gly Gln
        1205                1210                1215
Met Tyr Lys Gly Gly Tyr Thr Lys Phe Asp Val Ser Glu Thr Asp
        1220                1225                1230
Lys Asp Gly Lys Glu Ser Lys Val Val Lys Phe Arg Tyr Phe Thr
        1235                1240                1245
```

-continued

```
Asn Glu Gly Val Met Ala Lys Gly Val Thr Val Ile Asp Gly Phe
    1250                1255                1260
Thr Gln Tyr Phe Gly Glu Asp Gly Phe Gln Ala Lys Asp Lys Leu
    1265                1270                1275
Val Thr Phe Lys Gly Lys Thr Tyr Tyr Phe Asp Ala His Thr Gly
    1280                1285                1290
Asn Gly Ile Lys Asp Thr Trp Arg Asn Ile Asn Gly Lys Trp Tyr
    1295                1300                1305
Tyr Phe Asp Ala Asn Gly Val Ala Ala Thr Gly Ala Gln Val Ile
    1310                1315                1320
Asn Gly Gln Lys Leu Tyr Phe Asn Glu Asp Gly Ser Gln Val Lys
    1325                1330                1335
Gly Gly Val Val Lys Asn Ala Asp Gly Thr Tyr Ser Lys Tyr Lys
    1340                1345                1350
Glu Gly Phe Gly Glu Leu Val Thr Asn Glu Phe Phe Thr Thr Asp
    1355                1360                1365
Gly Asn Val Trp Tyr Tyr Ala Gly Ala Asn Gly Lys Thr Val Thr
    1370                1375                1380
Gly Ala Gln Val Ile Asn Gly Gln His Leu Tyr Phe Asn Ala Asp
    1385                1390                1395
Gly Ser Gln Val Lys Gly Gly Val Val Lys Asn Ala Asp Gly Thr
    1400                1405                1410
Tyr Ser Lys Tyr Asn Ala Ser Thr Gly Glu Arg Leu Thr Asn Glu
    1415                1420                1425
Phe Phe Thr Thr Gly Asp Asn Asn Trp Tyr Tyr Ile Gly Ala Asn
    1430                1435                1440
Gly Lys Ser Val Thr Gly Glu Val Lys Ile Gly Asp Asp Thr Tyr
    1445                1450                1455
Phe Phe Ala Lys Asp Gly Lys Gln Val Lys Gly Gln Thr Val Ser
    1460                1465                1470
Ala Gly Asn Gly Arg Ile Ser Tyr Tyr Tyr Gly Asp Ser Gly Lys
    1475                1480                1485
Arg Ala Val Ser Thr Trp Ile Glu Ile Gln Pro Gly Val Tyr Val
    1490                1495                1500
Tyr Phe Asp Lys Asn Gly Leu Ala Tyr Pro Pro Arg Val Leu Asn
    1505                1510                1515
```

HIGH TITER PRODUCTION OF HIGHLY LINEAR POLY (α 1,3 GLUCAN)

This application claims priority to the provisional application U.S. 61/532723 filed on Sep. 9, 2011.

FIELD OF INVENTION

This invention relates to the field of production of a structural polysaccharide. Specifically, it relates to production of poly(α1,3 glucan) via an enzymatic reaction in the presence of linear primers. More specifically, it relates to using a linear primer for production of highly linear poly(α1,3 glucan).

BACKGROUND

Cellulose, a polysaccharide formed from glucose via β(1, 4) glucoside linkages by natural processes (Applied Fiber Science, F. Happey, Ed., Chapter 8, E. Atkins, Academic Press, New York, 1979), has achieved commercial prominence as a fiber as a consequence of the many useful products derived therefrom. In particular, cotton, a highly pure form of naturally occurring cellulose, is well-known for its beneficial attributes in textile applications.

Cellulose exhibits sufficient chain extension and backbone rigidity in solution to form liquid crystalline solutions (U.S. Pat. No. 4,501,886). However, sufficient polysaccharide chain extension has hitherto been achieved primarily in β(1,4) linked polysaccharides. Any significant deviation from that backbone geometry in the glucan polysaccharide family lowers the chain rigidity below that required for the formation of an ordered lyotropic phase. Additionally, it is well-known that important commercial cellulosic fibers such as cotton and rayon increasingly present sustainability issues with respect to land use and environmental imprint.

It is therefore highly desirable to discover other glucose-based polysaccharides with utility in films, fibers and resins largely because of the current emphasis on producing low cost, structural materials from renewable resources. In addition such polymers offer materials that are environmentally benign throughout their entire life cycle.

Poly(α1,3 glucan), a glucan polymer characterized by having α(1,3) glycoside linkages, has been isolated by contacting an aqueous solution of sucrose with a glucosyltransferase (gtfJ) enzyme isolated from *Streptococcus salivarius* (Simpson et al., Microbiology, 141: 1451-1460, 1995). Glucan refers to a polysaccharide composed of D-glucose monomers linked by glycosidic bonds. Films prepared from poly(α1,3 glucan) tolerated temperatures up to 150° C. and provided an advantage over polymers obtained from β(1,4) linked polysaccharides (Ogawa et al., Fiber Differentiation Methods, 47: 353-362, 1980).

U.S. Pat. No. 7,000,000 disclosed preparation of a polysaccharide fiber comprising hexose units, wherein at least 50% of the hexose units within the polymer were linked via α(1,3) glycoside linkages using the gtfJ enzyme of *Streptococcus salivarius*. After derivatization, to the acetate ester, the disclosed polymer formed a liquid crystalline solution when it was dissolved above a critical concentration in a solvent or in a mixture comprising a solvent. From this solution continuous, strong, cotton-like fibers highly suitable for use in textiles were prepared and used either in a derivatized form or as a non-derivatized (regenerated) form. The complex and branched glucan, dextran, is used as a primer to initiate poly (α1,3 glucan) synthesis by glucosyltransferase enzymes. During polymerization dextran is incorporated into the structure of poly(α1,3 glucan) creating branches within the poly (α1,3 glucan). The presence of such regions in the poly(α1,3 glucan) can compromise the characteristics of the polymer during fiber spinning and in end use applications. It can therefore be desirable to identify primer molecules, without branches in their structures, which would allow synthesis of highly linear poly(α1,3 glucan) polymers.

SUMMARY OF INVENTION

This invention is a process for production of highly linear poly(α1,3 glucan) from a renewable feedstock, for applications in fibers, films, and pulps. The highly linear poly(α1,3 glucan) is made directly in a one-step enzymatic reaction using a recombinant glucosyltransferase enzyme as the catalyst, sucrose as the substrate and hydrolyzed poly(α1,3 glucan) as the primer. The highly linear poly(α1,3 glucan) polymer thus obtained does not contain undesired branches in its molecular chain and is therefore more amenable to preparing fibers with superior mechanical properties.

In one aspect, the disclosed invention relates to a process for the synthesis of a highly linear poly(α1,3 glucan) comprising an enzyme reaction solution comprising:
 a) sucrose;
 b) at least one glucosyltransferase enzyme; and
 c) at least one primer wherein said primer is hydrolyzed poly(α1,3 glucan);
wherein said primer initiates the synthesis of said highly linear poly(α1,3 glucan) through the action of the glucosyltransferase enzyme on the sucrose.

In another aspect, the disclosed invention is a process for preparing highly linear poly(α1,3 glucan) in a reaction system comprising two chambers, separated by a semi-permeable membrane, wherein:
 a) a first chamber comprises an enzyme reaction solution comprising:
  i) sucrose;
  ii) at least one glucosyltransferase enzyme; and
  iii) at least one primer wherein said primer is hydrolyzed poly(α1,3 glucan); and
 b) a second chamber, separated from the first chamber by a semi-permeable membrane in contact with the enzyme reaction solution wherein the semi-permeable membrane is permeable to fructose and other low molecular weight moieties but impermeable to poly(α1,3 glucan), facilitates continuous removal or dilution of fructose while retaining the poly(α1,3 glucan) inside the first chamber.

In another aspect, the disclosed invention is a composition comprising:
 a) sucrose;
 b) at least one glucosyltransferase enzyme; and
 c) at least one primer wherein said primer is hydrolyzed poly(α1,3 glucan);
wherein the composition is a reaction mixture useful for the synthesis of highly linear poly(α1,3 glucan).

DESCRIPTION OF DNA SEQUENCES

Figure 1:
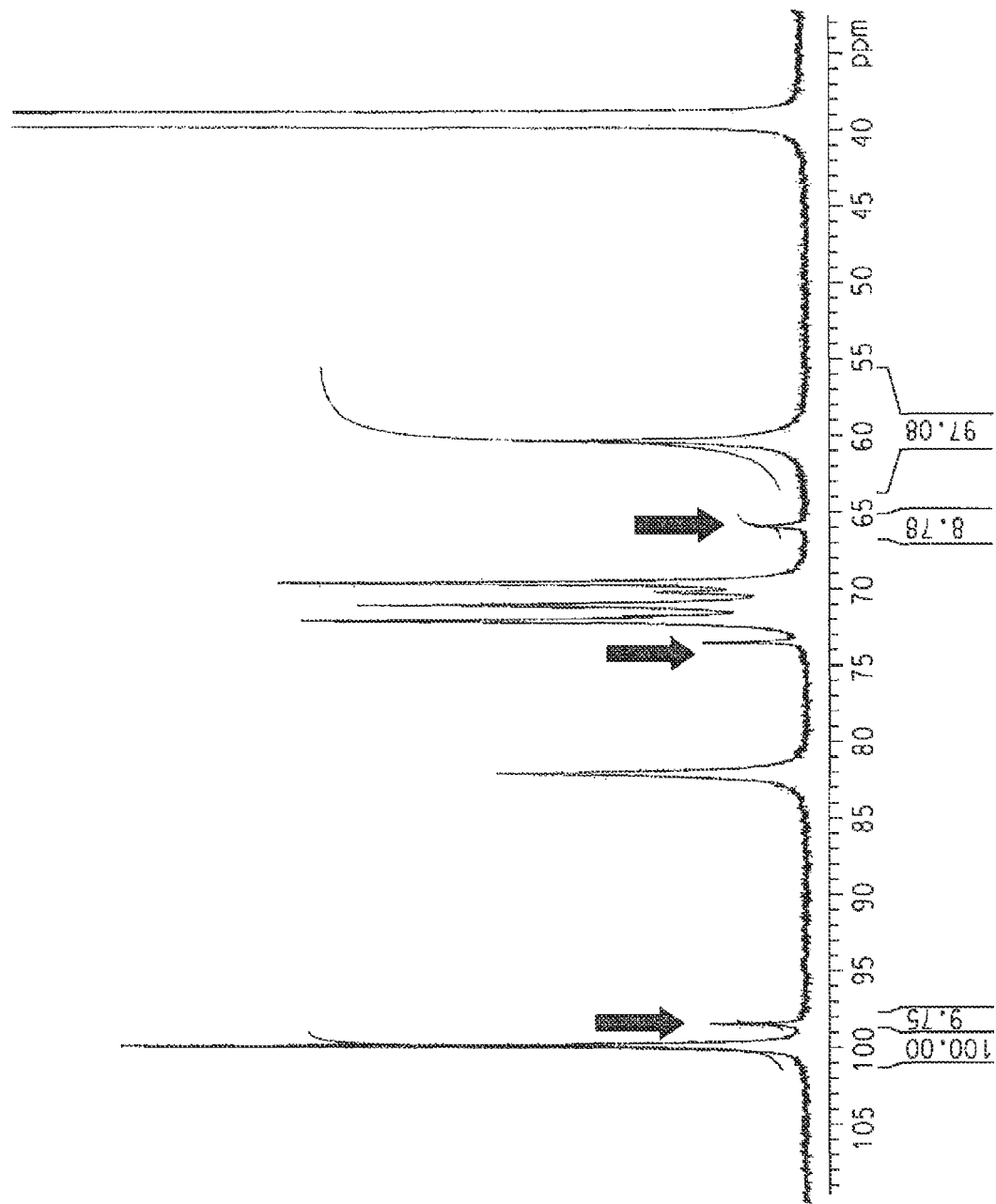
FIG. 1 depicts the $^{13}$C NMR spectrum of poly(α1,3 glucan) formed in a gtf enzyme reaction when dextran was used as the primer. The block arrows in FIG. 1 indicate resonances that result from incorporation of the dextran primer into the glucan polymer product.

SEQ NO. 1 is the DNA sequence of the synthesized gene of the mature glucosyltransferase which has been codon optimized for expression in E. coli.

SEQ NO. 2 is the DNA sequence for the plasmid pMP52.

SEQ NO. 3 is the amino acid sequence of the mature glucosyltransferase (gtfJ enzyme; EC 2.4.1.5; GENBANK® AAA26896.1) from Streptococcus salivarius (ATCC 25975).

DETAILED DESCRIPTION OF INVENTION

Poly(α1,3 glucan) is a potentially low cost polymer which can be enzymatically produced from renewable resources such as sucrose using the glucosyltransferase (gtfJ) enzymes of streptococci. Sucrose is converted to fructose, leucrose and poly(α1,3 glucan) during the gtf reaction. The term "glucosyltransferase (gtf) enzyme", as used herein, refers to an enzyme excreted by oral streptococci, such as Streptococcus salivarius, which utilizes the high free energy of the glycosidic bond of sucrose to synthesize poly(α1,3 glucan). The term "leucrose", as used herein, refers to a disaccharide consisting of glucose and fructose, linked by an α(1,5) bond. The term "poly(α1,3 glucan)", as used herein, refers to high molecular weight polymers resulting from linking glucose units via α(1,3) glycosidic linkages. A glycosidic bond can join two monosaccharides to form a disaccharide. The glycosidic bonds can be in the α or β configuration and can generate, for example, α(1,2), α(1,), α(1,4), α(1,6), β(1,2), β(1,3), β(1,4) or β(1,6) linkages. The term "α(1,3) glycoside linkage", as used herein, refers to a type of covalent bond that joins glucose molecules to each other through the ring carbons 1 and 3 on adjacent glucose rings.

For purposes of this invention, sufficient quantities of the gftJ enzyme can be produced using a recombinant E. coli strain for gtfJ production as described in the Examples. Methods for designing the codon optimized genes and expression in E. coli are well known in the art.

Methods for the growth of recombinant microorganisms are well known in the art. Recombinant microorganisms expressing the desired gtf enzyme to perform the instant reaction can be grown in any container, such as, for example: various types of flasks with and without indentations; any autoclavable container that can be sealed and temperature-controlled; or any type of fermenter. In one embodiment, production of the gtfJ enzyme for poly(α1,3 glucan) production in the present invention can be achieved by growing the recombinant E. coli MG1655/pMP52, expressing the gtfJ enzyme, in a fermenter.

The glucosyltransferase enzyme used in the present invention is the gtfJ (E.C. 2.4.1.5) enzyme of Streptococcus salivarius.

In one embodiment, the enzyme reaction solution can comprise only one gtf enzyme as described herein. In another embodiment, the enzyme reaction solution can comprise a combination of more than one type of gtf enzyme.

The terms "enzymatic reaction" and "enzyme reaction" are used interchangeably and refer to a reaction that is performed by the gtf enzyme. The term "enzyme reaction solution", as used herein, refers to a reaction solution comprising at least one gtf enzyme in a buffer solution comprising sucrose and optionally one or more primers to convert sucrose to poly (α1,3 glucan).

The gtfJ enzyme of Streptococcus salivarius, used as the catalyst for conversion of sucrose to poly(α1,3 glucan) in the current invention, is a primer-independent gtf enzyme. The primer-independent enzymes do not require the presence of a primer to perform the reaction. A primer-dependent gtf enzyme, as referenced in the present application, refers to a gtf enzyme that requires the presence of an initiating molecule in the enzyme reaction solution to act as a primer for the enzyme during poly(α1,3 glucan) synthesis. Thus a "primer", as the term is used herein, refers to any molecule that can act as the initiator for the primer-dependent glycosyltransferases. For the purposes of the present invention, either or both a primer-independent enzyme, and/or a primer-dependent gtf enzyme can be used in the same enzyme reaction system during poly(α1,3 glucan) synthesis.

While gtfJ is a primer-independent enzyme, it also performs the reaction in the presence of a primer. In the present invention, dextran, which is a complex, branched glucan was used as a primer for the gtfJ enzyme. Thus in an embodiment, the gtfJ reaction solution for production of poly(α1,3 glucan) does not comprise a primer. Alternatively, in another embodiment, the gtfJ reaction solution for production of poly(α1,3 glucan) comprises a primer.

Dextran, which is a complex, branched glucan is commonly used as the primer for various gtf primer-dependent enzyme reactions to convert sucrose to poly(α1,3 glucan). During the gtfJ enzyme reaction, dextran is incorporated into the structure of poly(α1,3 glucan). FIG. 1 depicts the $^{13}$C NMR spectrum of poly(α1,3 glucan) formed in a gtfJ reaction when dextran was used as the primer. The spectrum shows the presence of resonance peaks (in parts per million, ppm) at 99.58 (glucan), 98.17(dextran), 81.98 (glucan), 73.49 (dextran), 72.07 (glucan), 71.49 (dextran), 71.05 (glucan) 70.14 (dextran), 69.59 (glucan), 65.93 (dextran) and 60.29 (glucan), attributable to the incorporation of the dextran molecule into the structure of the poly(α1,3 glucan) formed during the enzymatic reaction.

Figure 2:
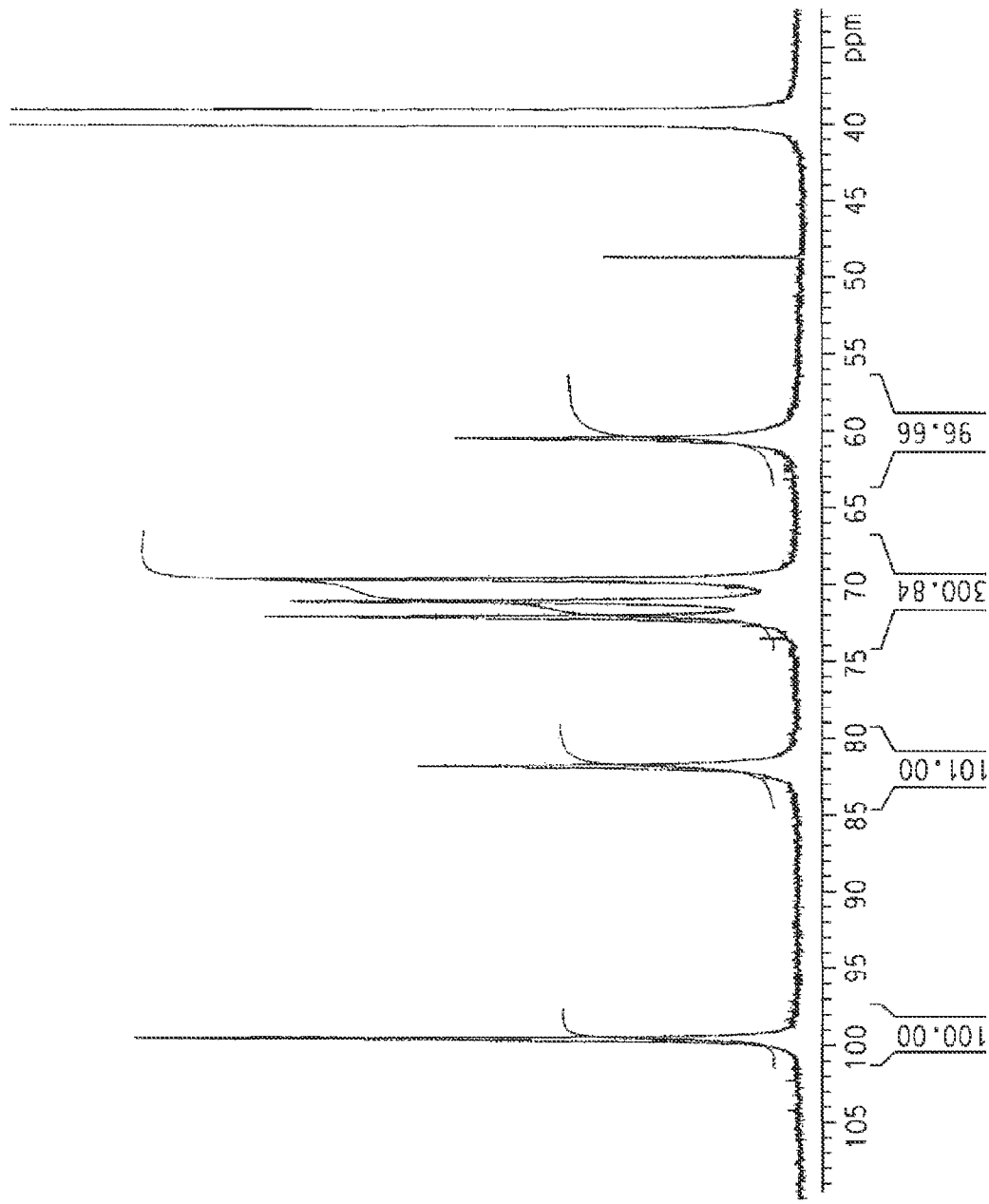
FIG. 2 depicts the $^{13}$C NMR spectrum of the highly linear poly(α1,3 glucan) synthesized from sucrose using oligomers of the hydrolyzed poly(α1,3 glucan) as a primer in the gtfJ enzyme reaction. The signature resonances, in FIG. 1, that showed incorporation of dextran primer in the poly(α1,3 glucan) are absent in this case.

The presence of such additional branches in the structure of poly(α1,3 glucan), when dextran is used as the primer for the gtfJ reaction, can compromise the fiber spinning process, fiber mechanical properties and end-use performance of poly (α1,3 glucan). Thus, attempts were made to discover novel primers for the gtfJ enzyme reaction that would not introduce additional branches into the structure of poly(α1,3 glucan). In the instant invention, a novel primer was used in the gtfJ enzymatic reaction solution for preparation of highly linear poly(α1,3 glucan) molecules that were largely devoid of undesired branches in their structures. The term "highly linear poly(α1,3 glucan)", as used herein, refers to a poly(α1,3 glucan) in which less than 2% of the glycoside linkages are branched. For this purpose, poly(α1,3 glucan) was hydrolyzed to produce oligomers of poly(α1,3 glucan). Hydrolysis of poly(α1,3 glucan) can be performed by various methods well-known in the relevant art. The hydrolyzed poly(α1,3 glucan) was then used as the primer for the gtfJ reaction. FIG. 2 depicts the $^{13}$C NMR spectrum of the highly linear poly (α1,3 glucan) synthesized from sucrose using oligomers of the hydrolyzed poly(α1,3 glucan) as the primer in the gtfJ enzyme reaction. As can be seen in the spectrum specific resonance peaks related to dextran at 98.15, 73.57, 71.63, 70.17, 65.79 and 60.56 ppm are absent. The only resonances in this sample can be seen at 99.51, 81.81, 72.06, 71.05, 69.61, and 60.32 ppm, thus indicating formation of a highly linear poly(α1,3 glucan) during the gtf reaction. Application of the highly linear poly(α1,3 glucan) can eliminate problems associated with the polymer when dextran is used as the primer.

The production of poly(α1,3 glucan), by the gtfJ enzyme of *Streptococcus salivarius* is inhibited by its by-product, fructose. When fructose accumulates in the enzyme reaction solution it can inhibit production of poly(α1, 3 glucan) presumably by competing for available glycosyl moieties which results in the formation of the disaccharide, leucrose. In the present invention, to reduce the effect on gtfJ of fructose, the fructose in the enzyme reaction solution is continuously removed to prevent its accumulation to inhibitory levels in the enzyme reaction solution. For the purposes of the current invention the reaction system comprises a semi-permeable membrane that separates the enzyme reaction solution, contained in the first chamber, comprising one or more gtf enzyme, one ore more primers and sucrose, from the surrounding buffer contained in the second chamber. The term "chamber" as used herein, refers to any container that can hold the enzyme reaction solution or the products of the enzyme reaction solution. The chamber can be made of glass, plastic, metal, film, membrane or any other type of inert material that can hold the enzyme reaction solution. The term "semi-permeable membrane", as used herein, refers to a membrane that will allow passage of certain molecules or ions by diffusion while retaining some other molecules. Essentially any semi-permeable membrane, with a molecular cutoff between 12,000 and 100,000 Daltons that will allow fructose and other low molecular weight moieties that can be present in the enzyme reaction solution to pass through while retaining the enzyme and poly(α1,3 glucan) can be suitable for use in the present invention. The term "other low molecular weight moieties" as used herein, refers to various compounds with molecular weights below 1000 Daltons that can be present in the enzyme reaction solution. Due to the removal of the by-product fructose from the enzyme reaction solution contained in the first chamber, leucrose formation is reduced.

In one embodiment of the present invention, dialysis tubing is used as the semi-permeable membrane to remove the by-product fructose from the enzyme reaction solution. In another embodiment of the present invention, the enzyme reaction is performed at 20° C. to 25° C. In yet another embodiment, the enzyme reaction is performed at 37° C.

Application of hydrolyzed poly(α1,3 glucan) as the primer for the gtfJ enzyme reaction did not have any negative impact on the titer of the poly(α1,3 glucan) formed during this reaction as compared to the titer of poly(α1,3 glucan) formed when dextran was used as the primer as described in Example 6. The instant disclosure provides for production of a novel poly(α1,3 glucan), as a low cost material that can be economically obtained from readily renewable sucrose feedstock for a variety of applications including fibers, films, and pulps. In particular, it is expected that poly(α1,3 glucan) fibers, for example, will functionally substitute for cotton and regenerated cellulose fibers, leading to new textile fibers with minimal environmental impact and excellent sustainability versus incumbents.

EXAMPLES

The invention is further described and illustrated in, but not limited to, the following specific embodiments.

Materials

Dialysis tubing (Spectrapor 25225-226, 12000 molecular weight cut-off) was obtained from VWR (Radnor, Pa.).

Dextran and ethanol were obtained from Sigma Aldrich.

Sucrose was obtained from VWR.

Suppressor 7153 antifoam was obtained from Cognis Corporation (Cincinnati, Ohio).

All other chemicals were obtained from commonly used suppliers of such chemicals.

The $^{13}C$ nuclear magnetic resonance ($^{13}C$ NMR) analyses were performed using a Bruker Avance 500 MHz NMR spectrometer (Bruler-Biospin Corporation, Bilerica, Mass.) equipped with a CPDuI cryoprobe.

Abbreviations Used:

"g/L" is gram(s) per liter; "mL" is milliliter(s);"mg" is milligram(s); "mg/mL" is milligram(s) per milliliter; "mL/L" is milliliters per liter; "w/w" is weight per weight; "w/v" is weight per volume; "rpm" is revolutions per minute; "nm" is nanometers; "OD" is optical density; "mM" is millimolar; "psi" is Pounds pressure per square inch; "slpm" is standard liters per minute; "g feed/min" is grams feed per minute; "IPTG" is isopropyl β-D-1-thiogalacto-pyranoside; "kDa" is killo Dalton; "BCA" is bicinchoninic acid.

Seed Medium

The seed medium, used to grow the starter cultures for the fermenters, contained: yeast extract (Amberx 695, 5.0 grams per liter, g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 using either 5N NaOH or $H_2SO_4$ and the medium was sterilized in the flask. Post sterilization additions included glucose (20 mL/L) of a 50% (w/w) solution and ampicillin (4 mL/L of a 25 mg/mL) stock solution).

Fermenter Medium

The growth medium used in the fermenter contained: $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Ambrex 695, 5.0 g/L), Suppressor 7153 antifoam (0.25 milliliters per liter, mL/L), NaCl (1.0 g/L), $CaCl_2$ dihydrate (10 g/L), and NIT trace elements solution (10 mL/L). The NIT trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose (12.5 g/L of a 50% w/w solution) and ampicillin (4 mL/L of a 25 mg/mL stock solution).

$^{13}C$ NMR Method for Analysis of Poly(α1,3 Glucan)

Poly(α1,3 glucan) (25-30 mg) was added to a vial and 1 mL of deuterated Dimethyl Sulfoxide, containing 3% by weight of Lithium Chloride, was added to it. The mixture was shaken and warmed with a heat gun until the glucan sample dissolved. A solution of the glucan polymer can also be made in deuterated Dimethyl Sulfoxide containing 10 mole % of an ionic liquid such as 1-ethyl-3-methyl imidazolium acetate. An aliquot (0.8 mL), of the solution was transferred with a glass pipet, into a 5 mm NMR tube. A quantitative $^{13}C$ NMR spectrum was acquired using a Bruker Avance 500 MHz NMR spectrometer equipped with a CPDuI cryoprobe. The spectrum was acquired at a spectral frequency of 125.76 MHz, using a spectral window of 26041.7 Hz, an inverse gated decoupling pulse sequence using waltz decoupling, an acquisition time of 0.629 sec., an inter-pulse delay of 5 sec., and 6000 pulses. The time domain data was transformed using exponential multiplication of 2.0 Hz.

Example 1

Construction of Glucosyltransferasxe (qtfJ) Enzyme Expression Strain

A gene encoding the mature glucosyltransferase enzyme (gtfJ; EC 2.4.1.5; GENBANK® AAA26896.1, SEQ ID NO:

3) from *Streptococcus salivarius* (ATCC 25975) was synthesized using codons optimized for expression in *E. coli* (DNA 2.0, Menlo Park Calif.). The nucleic acid product (SEQ ID NO: 1) was subcloned into pJexpress404® (DNA 2.0, Menlo Park Calif.) to generate the plasmid identified as pMP52 (SEQ ID NO: 2). The plasmid pMP52 was used to transform *E. coli* MG1655 (ATCC 47076™) to generate the strain identified as MG1655/pMP52. All procedures used for construction of the glucosyltransferase enzyme expression strain are well known in the art and can be performed by individuals skilled in the relevant art without undue experimentation.

Example 2

Production of Recombinant gtfJ in Fermentation

Production of the recombinant gtfJ enzyme in a fermenter was initiated by preparing a pre-seed culture of the *E. coli* strain MG1655/pMP52, expressing the gtfJ enzyme, constructed as described in Example 1. A 10 mL aliquot of the seed medium was added into a 125 mL disposable baffled flask and was inoculated with a 1.0 mL culture of *E. coli* MG1655/pMP52 in 20% glycerol. This culture was allowed to grow at 37° C. while shaking at 300 revolutions per minute (rpm) for 3 hours.

A seed culture, for starting the fermenter, was prepared by charging a 2 L shake flask with 0.5 L of the seed medium. 1.0 mL of the pre-seed culture was aseptically transferred into 0.5 L seed medium in the flask and cultivated at 37° C. and 300 rpm for 5 hours. The seed culture was transferred at $OD_{550\,nm}$>2 to a 14 L fermenter (Braun, Perth Amboy, N.J.) containing 8 L of the fermenter medium described above at 37° C.

Cells of *E. coli* MG1655/pMP52 were allowed to grow in the fermenter and glucose feed (50% w/w glucose solution containing 1% w/w $MgSO_4.7H_2O$) was initiated when glucose concentration in the medium decreased to 0.5 g/L. The feed was started at 0.36 g feed/min and increased progressively each hour to 0.42, 0.49, 0.57, 0.66, 0.77, 0.90, 1.04, 1.21, 1.41 1.63, 1.92, 2.2 g feed/min respectively. The rate remained constant afterwards. Glucose concentration in the medium was monitored using an YSI glucose analyzer (YSI, Yellow Springs, Ohio). When glucose concentration exceeded 0.1 g/L the feed rate was decreased or stopped temporarily. Induction of glucosyltransferase enzyme activity was initiated, when cells reached an $OD_{550}$ of 70, with the addition of 9 mL of 0.5 M IPTG. The dissolved oxygen (DO) concentration was controlled at 25% of air saturation. The DO was controlled first by impeller agitation rate (400 to 1200 rpm) and later by aeration rate (2 to 10 slpm). The pH was controlled at 6.8. $NH_4OH$ (14.5% w/v) and $H_2SO_4$ (20% w/v) were used for pH control. The back pressure was maintained at 0.5 bars. At various intervals (20, 25 and 30 hours), 5 mL of Suppressor 7153 antifoam was added into the fermenter to suppress foaming. Cells were harvested by centrifugation 8 hours post IPTG addition and were stored at −80° C. as a cell paste.

Example 3

Preparation of gtfJ Crude Enzyme Extract from Cell Paste

The cell paste obtained above was suspended at 150 g/L in 50 mM potassium phosphate buffer pH 7.2 to prepare a slurry. The slurry was homogenized at 12,000 psi (Rannie-type machine, APV-1000 or APV 16.56) and the homogenate chilled to 4° C. With moderately vigorous stirring, 50 g of a floc solution (Aldrich no. 409138, 5% in 50 mM sodium phosphate buffer pH 7.0) was added per liter of cell homogenate. Agitation was reduced to light stirring for 15 minutes. The cell homogenate was then clarified by centrifugation at 4500 rpm for 3 hours at 5-10° C. Supernatant, containing crude gtfJ enzyme extract, was concentrated (approximately 5×) with a 30 kDa cut-off membrane. The concentration of protein in the gftJ enzyme solution was determined by the BCA protein assay (Sigma Aldrich) to be 4-8 g/L.

Example 4

Production of Poly(α1,3 Glucan) for Preparation of Hydrolyzed Poly(α1,3 Glucan) to be Used as the Primer for the qtfJ Reaction An aqueous solution (190 L) consisting of sucrose (15 wt %), Dextran T-10 (569 g), ethanol and potassium phosphate buffer was prepared and adjusted to pH 6.8-7.0. This solution was then charged with 0.95 L (1 vol %) of the gtf enzyme extract. Table 1 shows the components of the enzyme reaction solution that was used in this experiment. The enzyme reaction solution was maintained at 20-25° C. for 72 hours. After this time the poly(α1,3 glucan) solids were collected on a Buchner funnel using a 325 mesh screen over a 40 micrometers filter paper. The filter cake was resuspended in deionized water and filtered twice more as above to remove sucrose, fructose and other low molecular weight soluble by-products. Finally two additional washes with methanol were carried out, the filter cake was pressed out thoroughly on the funnel and dried in vacuum at room temperature. A total of 3864 g of white flaky, solids of poly(α1,3 glucan) was obtained.

TABLE 1

Components of the enzyme reaction solution used for the synthesis of poly (α 1, 3 glucan)

| components | concentration |
| --- | --- |
| sucrose | 15 wt % |
| Dextran T-10 | 569 g |
| $KH_2PO_4$ | 9.5 L |
| 10% KOH | Adjust to pH 7.0 |
| gtf enzyme | 1 vol % |
| Ethanol | 19 L |
| De-ionized water | to 190 L |
| poly (α 1, 3 glucan) obtained | 3864 g |

Example 5

Hydrolysis of Poly(α1,3 Glucan)

Poly(α1,3 glucan) (10 g) was suspended in 500 mL of 37% HCl and stirred for 105 minutes at 20-25° C. Water (50 mL) was then added and the resulting suspension was treated by slowly adding sodium hydroxide pellets with cooling to neutralize the solution which was then dialyzed against water using a 500 molecular weight cut off membrane to remove the salt. The resulting liquid solution of hydrolyzed poly(α1,3 glucan), containing glucan oligomers (with some residual sodium chloride), was used directly as the primer for the enzymatic synthesis of highly linear poly(α1,3 glucan) as described below.

Example 6

Enzymatic Synthesis of Highly Linear Poly(α1,3 Glucan) Using Hydroloyzed Poly(α1,3 Glucan) as the Primer Eight liters of a sucrose stock solution (Table 2) was used for preparation of the gtf enzyme reaction solution.

TABLE 2

Components of the sucrose stock solution

| components | amount |
|---|---|
| sucrose | 1200 g |
| KH$_2$PO$_4$ buffer (pH 6.8-7.0) | 50 mM |
| 10% KOH | As needed for adjusting the pH to 7.0 |
| ethanol | 800 mL |
| De-ionized water | up to 8 liters |

Five individual dialysis tubes (50 mL capacity)(for each test set) were charged with 50 mL of the sucrose stock solution plus 2.0 volume % crude gtfJ enzyme, which was prepared as described above, and either 9 g of Dextran T-10 or 9 g of poly(α1,3 glucan), as primers for the gtfJ enzyme reaction and the tubes were sealed. Table 3 summarizes the various components present in the gtf enzyme reaction solution in the dialysis tubes.

TABLE 3

Components present in the gtf enzyme reaction solutions with different primers

| components | Hydrolyzed poly (α 1, 3 glucan) Rx | Dextran Rx |
|---|---|---|
| sucrose | 450 g | 450 g |
| primer | hydrolyzed glucan 9 g | Dextran 9 g |
| KH$_2$PO$_4$ Buffer (pH 6.8-7.0) | 50 mM | 50 mM |
| gtf enzyme | 2 vol % | 2 vol % |
| 10% KOH | as needed for adjusting to pH 7 | as needed for adjusting to pH 7 |
| Ethanol | 300 mL | 300 mL |
| De-ionized water | up to 3 liters | up to 3 liters |

The individual dialysis tubes, containing the enzyme reaction solution, were then suspended in a polyethylene bucket containing 2.75 liters of the sucrose stock solution (Table 2) as the surrounding buffer. The buckets were placed on a magnetic stirring plate and allowed to stir at 20-25° C. for 72 hours. Individual dialysis tubes were removed at various timed intervals for determination of the amount of poly(α1,3 glucan) formed in each tube.

After removal from the bucket the dialysis tubes were cut open and the poly(α1,3 glucan) solids were obtained and dried as described in Example 4. The resulting dry weights of the poly(α1,3 glucan) from the test and the control samples at various time intervals are shown in Table 4.

TABLE 4

Production of poly (α 1, 3 glucan) using either dextran or hydrolyzed poly (α 1, 3 glucan) as primers in the gtfJ reaction

| Time (hours) | Test Using hydrolyzed poly (α 1, 3 glucan) as primer (g) | Control Using Dextran as primer (g) |
|---|---|---|
| 4 | 0.15 | 0.31 |
| 24 | 1.20 | 1.18 |
| 48 | 2.54 | 2.47 |
| 96 | 4.92 | 4.85 |
| 168 | 6.50 | 7.73 |

The poly(α1,3 glucan) samples thus obtained were subsequently characterized by $^{13}$C NMR spectroscopy to analyze for polymer backbone linkages. In FIG. 1 which shows the $^{13}$C NMR spectrum of the poly(α1,3 glucan) formed using dextran as the primer, resonances (ppm) at 99.58 (glucan), 98.17(dextran), 81.98 (glucan), 81.98, 73.49 (dextran), 72.07 (glucan), 71.05 (glucan) 70.14 (dextran), 69.59 (glucan), 65.93 (dextran) and 60.29 (glucan), attributable to incorporation of the dextran molecule into the structure of the poly (α1,3 glucan) formed during the enzymatic reaction. The dextran resonances are consistent with the incorporation of branched (α1,6) glycoside linkages into the structure of poly (α1, 3 glucan).

In contrast, in FIG. 2, which shows the $^{13}$C NMR spectrum of the poly(α1,3 glucan) when hydrolyzed poly(α1,3 glucan) served as the primer, as expected, only six carbon signals were detected in the final product at 99.51, 81.81, 72.06, 71.05, 69.61, and 60.32 ppm showing the absence of any branches in the structure of this poly(α1,3 glucan).

This example clearly illustrates that comparable titers can be obtained during the gtf reaction using either the dextran or the hydrolyzed poly(α1,3 glucan) as primers and demonstrates the possibility of obtaining high titers of the highly linear poly(α1,3 glucan).

Example 7

Enzymatic Synthesis of Highly Linear Poly(α1,3 Glucan) Using Hydroloyzed Poly(α1,3 Glucan) as the Primer at 37° C.

The composition of the enzyme reaction solutions used for this Example is shown in Table 5. Five individual dialysis tubes (50 mL capacity) (for each test set) were charged with 50 mL of the enzyme reaction solution and were sealed.

TABLE 5

Components of the enzyme reaction solutions at 37° C.

| components | test | control |
|---|---|---|
| sucrose | 450 g | 450 g |
| Dextran T-10 | 0 | 3 g/L |
| Hydrolyzed poly (α1, 3 glucan) | 3 g/L | 0 |
| KH$_2$PO$_4$ buffer | As needed | As needed |
| 10% KOH | As needed | As needed |
| gff enzyme | 1 vol % | 3 vol % |
| ethanol | 300 mL | 300 mL |
| De-ionized water | up to 3 L | up to 3 L |
| Temperature | 37° C. | 37° C. |

The individual dialysis tubes were then suspended in a polyethylene bucket containing 2.75 L of the sucrose stock solution (Table 2) as the surrounding buffer and the buckets were placed in an incubator at 37° C. The individual dialysis tubes were removed at various timed intervals and the reaction products were isolated as described above. The resulting dry weights of the poly(α1,3 glucan) obtained in the test and the control samples are shown in Table 6.

TABLE 6

Amount of poly (α 1, 3 glucan) obtained in test and control samples

| Time (hours) | Test (g) | Control (g) |
|---|---|---|
| 4 | 0.15 | 1.25 |
| 24 | 1.12 | 4.34 |
| 48 | 2.54 | 6.34 |
| 96 | 4.92 | ND |
| 168 | 6.50 | ND |

ND = not determined

Samples of poly(α1,3 glucan) obtained in the test and the control were subsequently characterized by $^{13}$C NMR spectroscopy. In the poly(α1,3 glucan) obtained from the test sample with hydrolyzed poly(α1,3 glucan) as the primer, there were only the six expected discrete carbon atoms at 99.46, 81.66, 72.13, 71.09, 69.66, and 60.30 ppm while in the control sample additional carbon atoms (shown as block arrows in FIG. 1), consistent with the incorporation of branched poly(α1,6) glycoside linkages, were present. This example clearly illustrates that highly linear poly(α1,3 glucan) can be readily obtained using hydrolyzed poly(α1,3 glucan) as the primer for the gtfJ reaction performed at 37° C.

What is claimed is:

1. A process for the synthesis of a highly linear poly(α1,3 glucan), wherein the process comprises providing an enzyme reaction solution comprising:
   a) sucrose;
   b) at least one glucosyltransferase enzyme; and
   c) at least one primer wherein said primer is hydrolyzed poly(α1,3 glucan);
wherein said primer initiates the synthesis of said highly linear poly(α1,3 glucan) through the action of the glucosyltransferase enzyme on the sucrose.

2. The process of claim 1 wherein the poly(α1,3 glucan) formed does not contain branches in its structure.

3. The process of claim 2 wherein the glucosyltransferase enzyme is gtfJ from *Streptococcus salivarius*.

4. The process of claim 1 wherein the at least one glucosyltransferase enzyme is a primer-independent enzyme.

5. The process of claim 1 wherein the at least one glucosyltransferase enzyme is a primer-dependent enzyme.

6. The process of claim 1 wherein more than one glucosyltransferase enzyme is present in the enzyme reaction solution.

7. The process of claim 6 wherein the more than one glucosyltransferase enzyme comprises a mixture of at least one primer-dependent enzyme and at least one primer-independent enzyme.

8. A reaction system comprising two chambers, separated by a semi-permeable membrane, wherein:
   a) a first chamber comprises an enzyme reaction solution comprising:
      i) sucrose;
      ii) at least one glucosyltransferase enzyme; and
      iii) at least one primer wherein said primer is hydrolyzed poly (α1,3 glucan); and
   b) a second chamber that is separated from the first chamber by a semi-permeable membrane in contact with the enzyme reaction solution, wherein the semi-permeable membrane (i) is permeable to fructose and other low molecular weight moieties but impermeable to highly linear poly(α1,3 glucan), and (ii) facilitates continuous removal of fructose while retaining said polymer inside the first chamber, wherein highly linear poly(α1,3 glucan) is produced in the reaction solution.

9. The reaction system of claim 8 wherein the semi-permeable membrane facilitates accumulation of the highly linear poly($\alpha$1,3 glucan) to a concentration ranging from 50 grams per liter to 300 grams per liter.

10. The reaction system of claim 8 wherein the semi-permeable membrane has a molecular weight cut-off from 12,000 to 100,000 Daltons.

11. The reaction system of claim 8 wherein the semi-permeable membrane is a dialysis tubing.

12. The reaction system of claim 8 wherein the glucosyltransferase enzyme is gtfJ from *Streptococcus salivarius*.

13. The reaction system of claim 8 wherein the glucosyltransferase enzyme is a primer-independent enzyme.

14. The reaction system of claim 8 wherein the glucosyltransferase enzyme is a primer-dependent enzyme.

15. The reaction system of claim 8 wherein more than one glucosyltransferase enzyme is present in the enzyme reaction solution.

16. The reaction system of claim 15 wherein the more than one glucosyltransferase enzyme comprises a mixture of at least one primer-dependent enzyme and at least one primer-independent enzyme.

17. A composition comprising:
    a) sucrose;
    b) at least one glucosyltransferase enzyme; and
    c) at least one primer wherein said primer is hydrolyzed poly($\alpha$1,3 glucan);
wherein the composition is a reaction mixture useful for the synthesis of a highly linear poly($\alpha$1,3 glucan).

\* \* \* \* \*